United States Patent
Perring et al.

(10) Patent No.: US 6,172,037 B1
(45) Date of Patent: Jan. 9, 2001

(54) PERFUME FIXATIVES COMPRISING POLYVINYLPYRROLIDONE AND HYDROXYPROPYL CELLULOSE

(75) Inventors: Keith D. Perring, Ashford; Pamela V. Irving, Folkestone; Jeremy N. Ness; Kathleen M. Tuck, both of Ashford, all of (GB)

(73) Assignee: Quest International B.V., Naarden (NL)

( * ) Notice: Under 35 U.S.C. 154(b), the term of this patent shall be extended for 0 days.

(21) Appl. No.: 09/424,299

(22) PCT Filed: May 14, 1998

(86) PCT No.: PCT/GB98/01381

§ 371 Date: Nov. 22, 1999

§ 102(e) Date: Nov. 22, 1999

(87) PCT Pub. No.: WO98/52527

PCT Pub. Date: Nov. 26, 1998

(30) Foreign Application Priority Data

May 21, 1997 (EP) .................................... 97303459

(51) Int. Cl.⁷ ................................ A61K 7/46; A61L 9/04
(52) U.S. Cl. ............................................... 512/2; 424/76.4
(58) Field of Search ................................ 512/2; 424/76.4

(56) References Cited

PUBLICATIONS

Data Base WPI, Week 8540, Derwent Publications Ltd., AN 85–247016, XP002043726, "Flavouring camphor or naphthalene–by adding perfume contg. dissolved PVP or hydroxypropyl cellulose", JP 60 163 802 A, Aug. 26, 1985.

Data Base WPI, Week 8524, Derwent Publications Ltd., AN 85–144086, XP002043727, "Giving strong scent to insecticidal para–dichlorobenzene–using perfume soln. of PVP or hydroxypropyl cellulose", JP 60 078 926 A, May 4, 1985.

Data Base WPI, Week 8726 Derwent Publications Ltd., AN 87–183168, XP002043728, "Prepn. of long–lasting fragrance–contg. hydroxypropylcellulose ethanol and/or methanol soln. and vinylpyrrolidone", & JP 62 114 909 A, May 26, 1987.

Data Base WPI, Week 9511, Derwent Publications Ltd., AN 95–078134, XP002043729, "Resin compsn contg. aromatic component for imparting aroma to e.g. perfume–advertising goods—comprises water–soluble resin e.g. CMC, solvent for resin and aromatic component enclosed in microcapsule", JP 07 003 075 A, Jan. 6, 1995.

Data Base WPI, Week 8747, Derwent Publications Ltd., AN 87–331354, XP002043730, "Water–absorptive compsn. contg. perfume–comprises perfume coated with water soluble resin powder and water absorptive resin powder", & JP 62 236 860 A, Oct. 16., 1987.

Primary Examiner—Jill Warden
Assistant Examiner—Monique T. Cole
(74) Attorney, Agent, or Firm—Pillsbury Madison & Sutro LLP

(57) ABSTRACT

A perfume fixative consisting essentially of polyvinylpyrrolidone, hydroxy propyl cellulose and hydrophobic oil. The perfume fixative is being incorporated in a perfume-containing formulation or product. The fixative is found to be effective in enhancing perfume life, even when utilized at low levels.

13 Claims, No Drawings

PERFUME FIXATIVES COMPRISING POLYVINYLPYRROLIDONE AND HYDROXYPROPYL CELLULOSE

This application is the national phase of international application PCT/GB98/01381 filed May 14, 1998 which designated the U.S.

FIELD OF THE INVENTION

This invention concerns perfume fixatives, that is, compositions intended for use in perfume-containing formulations to enhance fragrance life. The words "perfume" and "fragrance" are used synonymously in this specification and no significance should be attached to the choice of word used in any particular context. The invention includes within its scope perfume fixatives, mixtures of perfume and fixative, mixtures of product base and fixative, and perfumed products including perfume and fixative.

BACKGROUND OF THE INVENTION

Fragrances in some products such as perfumed leave-on skin products, particularly (but not exclusively) ethanol-based ones eg (deo)colognes, personal perfumes, antiperspirant deodorants, hair colognes etc, tend to lose their character rapidly ie the top/middle notes evaporate. There is a desire to extend the life of such perfumes, particularly in retaining the initial character and intensity of the fragrance, and various perfume fixatives have been proposed. It is an important practical consideration that the fixative should not adversely affect the aesthetic character of the product, ie the fixative should not be discernible by the user.

PRIOR ART

Various fixative systems have been proposed including fixative oils (eg GLUCAM P20 (GLUCAM is a Trade Mark)) or film-forming polymers. The former require the use of relatively high levels of oil to produce noticeable effects, whilst when the latter are effective they produce very noticeable films (both visual and tactile). Various perfume carriers/encapsulates have also been proposed but suffer from problems with cost and visibility in the product and/or on the skin/hair. JP 62114909 discloses use of 1 to 60 wt % of polyvinylpyrrolidone (PVP) and 1 to 30 wt % of hydroxypropyl cellulose (HPC) with a fragrance material to produce a long lasting fragrance. Such levels of PVP and HPC would be very readily noticeable to the consumer.

SUMMARY OF THE INVENTION

In one aspect the present invention provides a perfume fixative comprising:

(a) polyvinylpyrrolidone;
(b) hydroxypropyl cellulose; and
(c) hydrophobic oil.

Polyvinylpyrrolidone (PVP) is readily commercially available in a range of molecular weights. The molecular weight of the PVP is not critical, but in general it is thought that PVP of higher molecular weights gives better performance. Good results have been obtained with the high molecular weight PVP LUVISKOL K90 (LUVISKOL is a Trade Mark) from BASF. A mixture of different PVPs may be used.

Hydroxypropyl cellulose (HPC) is similarly readily commercially available in a range of molecular weights. Higher molecular weight HPC gives better performance but also has a thickening effect, so it is preferred to use medium molecular weight HPCs as a compromise between performance and product compatibility. Good results have been obtained with KLUCEL G (KLUCEL is a Trade Mark) from Aqualon. A mixture of different HPCs may be used.

The hydrophobic oil should be non-ionic oil which is liquid at skin temperature (typically about 35° C. under normal conditions).

The hydrophobic oil suitably has an octanol/water partition co-efficient (log P) greater than 3, preferably greater than 5.

The hydrophobic oil suitably has a Hildebrand's solubility parameter ($\delta_{HILD}$) (Hildebrand, J. H. & Scott, R. L. The Solubility of Nonelectrolytes, 3rd edition, Reinhold, New York, 1950) of less than 20 MPa$^{1/2}$, and preferably greater than 14 MPa$^{1/2}$.

For obvious reasons, the hydrophobic oil should be odourless, of low odour, or of neutral or inoffensive odour.

The hydrophobic oil should also be non-volatile, preferably having a vapour pressure of less than about 0.01 mm Hg.

The hydrophobic oil is preferably an ester and/or (poly) ether. Esters are currently the most preferred materials.

Suitable hydrophobic oils include:

Propylene glycol dicaprate/dicaprylate, ie C8, C10 diester with propylene glycol, eg as MIGLYOL 840 (MIGLYOL is a Trade Mark) from Huls.

Dioctyl adipate

Isopropyl myristate

Glycerol monooleate

POE(10) cetyl ether

POE(20) sorbitan monolaurate

Dibutyl phthalate

Acetyl tributyl citrate

POE is an abbreviation for poly(oxyethylene) ether.

The currently preferred material is MIGLYOL 840.

A mixture of hydrophobic oils may be used.

The proportions of the 3 ingredients in the fixative are not critical.

Preferably the PVP and HPC together constitute at least 30%, more preferably at least 40%, by weight of the total weight of the fixative.

The oil preferably constitutes at least 10% by weight of the total weight of the fixative.

The composition typically comprises equal amounts by weight of PVP and HPC but this is not essential, and there may be cases where it is advantageous for the amount by weight of the HPC to exceed that of PVP.

Good results have been obtained with fixatives comprising, by weight, 25% PVP, 25% HPC and 50% hydrophobic oil.

A typical fixative formulation consists of:

MIGLYOL 840 50.0 wt % non-volatile oil

LUVISKOL K90 25.0 wt % PVP, high molecular weight

KLUCEL G 25.0 wt % HPC, medium molecular weight

The perfume fixative is used by being incorporated in a perfume-containing formulation or product. The fixative is found to be effective in enhancing perfume life, even when the fixative is used at low levels. The efficacy even at low levels is surprising and unexpected, and the reason for this efficacy is not yet known.

For practical reasons, the PVP and HPC together should not constitute more than about 0.5%, preferably not more than about 0.25%, by weight of the perfume-containing product. If these materials are present at higher levels they are discernible by the user, either by sight or feel, which is undesirable. However, the fixative is found to be effective in an amount corresponding to this constraint and also at lower levels.

For example, for a perfumed product containing 1% by weight perfume (which is typical of the perfume levels in a deodorant), a perfume:fixative weight ratio of at most 2:1 satisfies the above preferred constraint (for a fixative comprising 50% by weight PVP and HPC), and this is found to be more than adequate to obtain good results. Indeed, useful effects are obtained with considerably smaller amounts of fixative, eg with perfume:fixative weight ratios of 9:1 or even 19:1 which correspond to combined PVP and HPC weights of 0.055% and 0.026%, respectively (for a fixative comprising 50% by weight PVP and HPC).

For perfumed products with higher perfume levels, such as personal perfumes and fine fragrances which typically contain perfume in an amount in the range 2 to 25 % by weight, even higher perfume:fixative weight ratios can be effective.

The most effective level of the fixative depends upon the nature of the perfume and the amount in which it is used, and this can be determined by experiment.

The fixative may be used with a wide range of perfumes, although best results are obtained with perfumes that are not very substantive, ie those perfumes that are most in need of improvement.

For incorporation in a perfume or perfumed product, the fixative may be pre-mixed with perfume and then added to product base (which is all product ingredients except perfume). Alternatively the fixative may be added to the perfumed product (ie product base and perfume). As a further possibility, the fixative may be added to the product base, and perfume then added.

In a further aspect, the invention thus provides perfume mixed with perfume fixative in accordance with the invention.

The invention also covers a product base mixed with perfume fixative in accordance with the invention.

Another aspect of the invention covers a perfumed product comprising perfume fixative in accordance with the invention.

The invention is applicable to a wide range of perfumed products where fragrance life is a consideration, including perfumed leave-on skin products, including ethanol-, water- and silicone-based products, such as colognes, deo-colognes, personal perftnes, deodorant, antiperspirant deodorants, hair colognes etc.

A typical deodorant has the following composition:

| Ethanol | 80.0 wt % |
| Water | to 100.0 wt % |
| Fragrance | 1.00 wt % |
| Fixative Blend | 0.50 wt % |
| Trielosan | 9.25 wt % |

The fixative conveniently comprises, by weight, 50% MIGLYOL 840, 25% LUVISKOL K90 and 25 % KLUCEL G, as discussed above.

The invention will be further described, by way of illustration, in the following Examples.

EXAMPLE 1
(Cologne)

The following example illustrates the improvement in performance that can be produced using a classic citrus cologne perfume. The perfume tested comprised the following ingredients:

| Citrus Cologne Perfume A | wt % |
|---|---|
| Nonanal | 0.2 |
| Decanal | 0.4 |
| Benzyl Acetate | 5.0 |
| Camphor | 0.4 |
| Cineole | 0.4 |
| Citral Lemarome | 0.7 |
| Geraniol | 5.0 |
| Hydroxycitronellal | 2.0 |
| Limonene Dextro | 40.0 |
| Linalol | 10.0 |
| Linalyl Acetate | 16.0 |
| Lyral (IFF) | 2.0 |
| Methyl Dihydro Jasmonate Super (Q) | 2.0 |
| Myrcenyl Acetate | 3.0 |
| Terpinyl Acetate | 12.9 |
| (G) - Givaudan-Roure SA | |
| (Q) - Quest | |

Three colognes were prepared by simple mixing as follows:

| wt % | Reference | Test 1 | Test 2 | Test 3 |
|---|---|---|---|---|
| Citrus Cologne Perfume | 2.0 | 2.0 | 2.0 | 2.0 |
| Ethyl alcohol | 79.6 | 78.8 | 78.8 | 78.8 |
| Distilled water | 18.4 | 18.2 | 18.2 | 18.2 |
| LUVISKOL K90 | — | 0.25 | 0.25 | 0.5 |
| KLUCEL G | — | 0.25 | 0.25 | 0.5 |
| MIGLYOL 840 | — | 0.50 | — | — |
| MYVEROL 18-99 | — | — | 0.50 | — |

MYVEROL 18-99 (MYVEROL is a Trade Mark) is mainly glycerol mono-oleate and is available from Quest International.

The colognes were tested by a paired comparison test where 50 µl of each sample was placed using a calibrated pipette onto marked areas of a subject's forearms (one sample per arm!), all of whom were expert perfume evaluators. The test colognes were self-assessed by each subject after one and four hours relative to their reference colognes and the following average scores were obtained (0–5 scale):

| Average of 5 Subjects | Reference* | Test 1 | Comments |
|---|---|---|---|
| One Hour | 3.0 | 4.1 | Noticeably stronger and fresher |
| Four Hours | 2.0 | 2.7 | Stronger, more citrus odour |

| Average of 5 Subjects | Reference* | Test 2 | Comments |
|---|---|---|---|
| One Hour | 3.0 | 3.5 | Stronger and fresher top-note |
| Four Hours | 2.0 | 2.8 | Much stronger |

| Average of 5 Subjects | Reference* | Test 3 | |
|---|---|---|---|
| One hour | 3.0 | 3.5 | |
| Four hours | 2.0 | 2.5 | |

*Scores fixed for reference

EXAMPLE 2
(Aerosol)

Test 3 illustrates a fixative:perfume level of 1:2

Test 4 illustrates the same fixative but at 1:9 fixative:perfume

Test 5 illustrates a slightly changed fixative at ~1:19 fixative:perfume
The following solutions were prepared:

| wt % | Reference | Test 3 | Test 4 | Test 5 |
|---|---|---|---|---|
| Perfume AP209* | 1.0 | 1.0 | 1.0 | 1.0 |
| Ethyl alcohol | 99.0 | 98.5 | 98.89 | 98.95 |
| LUVISKOL K90 | — | 0.125 | 0.028 | 0.016 |
| KLUCEL G | — | 0.125 | 0.028 | — |
| MIGLYOL 840 | — | 0.25 | 0.056 | 0.032 |
| KLUCEL E (Low Molecular weight HPC) | — | — | — | 0.006 |

*available from Quest

These solutions were then made up into standard aerosols using a propellant:solution ratio of 65:35, where the propellant was a standard propane/butane mix. The aerosols were then tested in an analogous manner to the colognes, but using a fixed spray time 3 seconds at a fixed distance of 15 cm from the arm.

| Average of 5 Subjects | Reference | Test 3 | Comments |
|---|---|---|---|
| Initial | 4.8 | 4.9 | |
| One Hour | 3.6 | 3.8 | |
| Four Hours | 2.3 | 2.9 | Reference flat in comparison |
| Eight Hours | 0.6 | 1.5 | Almost nothing left of the reference |

| Average of 5 Subjects | Reference | Test 4 | Comments |
|---|---|---|---|
| Initial | 4.5 | 4.9 | |
| One Hour | 3.8 | 4.3 | |
| Four Hours | 2.5 | 3.3 | Clear difference in strength/freshness |
| Eight Hours | 1.5 | 2.2 | Still an impressive difference |

| Average of 5 Subjects | Reference | Test 5 | Comments |
|---|---|---|---|
| Initial | 5.0 | 4.9 | |
| One Hour | 3.8 | 3.8 | |
| Four Hours | 1.2 | 2.0 | Test 5 much fresher |
| Eight Hours | 0.5 | 1.0 | Clear difference |

What is claimed is:

1. A perfume fixative consisting essentially of:
   (a) polyvinylpyrrolidone;
   (b) hydroxypropyl cellulose; and
   (c) a non-volatile hydrophobic oil having a vapour pressure of less than about 0.01 mm Hg.

2. A perfume fixative according to claim 1, wherein the hydrophobic oil is selected from the group consisting of an ester and (poly)ether.

3. A perfume fixative according to claim 2, wherein the hydrophobic oil comprises one or more selected from the following:

Propylene glycol dicaprate/dicaprylate
   Dioctyl adipate
   Isopropyl myristate
   Glycerol monooleate
   POE(10) cetyl ether
   POE(20) sorbitan monolaurate
   Dibutyl phthalate
   Acetyl tributyl citrate.

4. A perfume fixative according to any one of the preceding claims, wherein the polyvinylpyrrolidone and hydroxypropyl cellulose together constitute at least 30%, preferably at least 40%, by weight of the total weight of the fixative.

5. A perfume mixed with an effective amount of perfume fixative in accordance with claim 1.

6. A perfumed product comprising an effective amount of perfume fixative in accordance with claim 1.

7. A perfumed product according to claim 6, wherein the polyvinylpyrrolidone and hydroxypropyl cellulose in the fixative together constitute no more than about 0.5%, preferably no more than about 0.25%, by weight of the total weight of the perfumed product.

8. The method which comprises providing a perfumed leave-on skin product containing the perfume fixative of claim 1 and applying said perfumed leave-on skin product to human skin.

9. A method of preparing a perfume or a perfumed product comprising providing a perfume fixative according to claim 1 and mixing an effective amount of said perfume fixative with a perfume.

10. A method according to claim 9 wherein the perfume or perfumed product is a leave-on skin product.

11. A perfume fixative according to claim 4 wherein the polyvinylpyrrolidone and hydroxypropyl cellulose together constitute at least 40% by weight of the total weight of the fixative and the balance is a hydrophobic oil selected from the group consisting of Propylene glycol dicaprate/dicaprylate
   Dioctyl adipate
   Isopropyl myristate
   Glycerol monooleate
   POE(10) cetyl ether
   POE(20) sorbitan monolaurate
   Dibutyl phthalate
   Acetyl tributyl citrate.

12. A perfumed product according to claim 6 wherein the polyvinylpyrrolidone and hydroxypropyl cellulose together constitute no more than about 0.25% by weight of the total weight of the perfumed product.

13. A perfume fixative according to claim 1 containing 25% polyvinylpyrrolidone, 25% hydroxypropyl cellulose and 50% hydrophobic oil.

* * * * *